United States Patent
Haubs et al.

(10) Patent No.: US 9,469,624 B2
(45) Date of Patent: Oct. 18, 2016

(54) INTEGRATED PROCESS FOR PRODUCING CYCLIC ACETALS AND OXYMETHYLENE POLYMERS

(71) Applicant: Ticona GMBH, Sulzbach (Taunus) (DE)

(72) Inventors: Michael Haubs, Bad Kreuznach (DE); Michael Hoffmockel, Niedernhausen (DE); Klaus Kurz, Kelsterbach (DE); Jurgen Lingnau, Mainz Laubenheim (DE); Damian Feord, Strasbourg (FR)

(73) Assignee: Ticona GmbH, Sulzbach (Taunus) (DE)

(*) Notice: Subject to any disclaimer, the term of this patent is extended or adjusted under 35 U.S.C. 154(b) by 104 days.

(21) Appl. No.: 14/359,314

(22) PCT Filed: Nov. 23, 2012

(86) PCT No.: PCT/EP2012/073541
§ 371 (c)(1),
(2) Date: May 20, 2014

(87) PCT Pub. No.: WO2013/076288
PCT Pub. Date: May 30, 2013

(65) Prior Publication Data
US 2014/0329988 A1    Nov. 6, 2014

Related U.S. Application Data

(60) Provisional application No. 61/718,393, filed on Oct. 25, 2012, provisional application No. 61/718,557, filed on Oct. 25, 2012.

(30) Foreign Application Priority Data

Nov. 24, 2011  (EP) .................................. 11190567
Nov. 24, 2011  (EP) .................................. 11190574
Nov. 24, 2011  (EP) .................................. 11190586

(51) Int. Cl.
C08G 59/00    (2006.01)
C07D 323/06   (2006.01)
(Continued)

(52) U.S. Cl.
CPC ............. *C07D 323/06* (2013.01); *C07C 47/04* (2013.01); *C07D 323/04* (2013.01); *C08G 2/10* (2013.01);
(Continued)

(58) Field of Classification Search
CPC ...... C07D 323/06; C08G 2/10; C08G 65/06; C08G 65/16
USPC ......................................................... 528/403
See application file for complete search history.

(56) References Cited

U.S. PATENT DOCUMENTS 3,305,529 A    2/1967  Reynolds et al.
3,457,227 A    7/1969  Kennedy
(Continued)

FOREIGN PATENT DOCUMENTS

AT      252913       3/1967
CN     101665409     3/2010
(Continued)

OTHER PUBLICATIONS

International Search Report and Written Opinion for application PCT/EP2012/073541 dated Apr. 15, 2013.
(Continued)

*Primary Examiner* — Shane Fang
(74) *Attorney, Agent, or Firm* — Dority & Manning, P.A.

(57) ABSTRACT

A process for producing cyclic acetals is described. A formaldehyde source is contacted with an aprotic compound in the presence of a catalyst to produce the cyclic acetals. The aprotic compound can increase conversion rates and/or efficiency. In one embodiment, the formaldehyde source is obtained from methanol. In particular, methanol can be converted into formaldehyde which is then converted into a cyclic acetal. In one embodiment, the cyclic acetal can then be used to produce oxymethylene polymers.

20 Claims, 1 Drawing Sheet

(51) Int. Cl.
*C08G 2/10* (2006.01)
*C08G 2/36* (2006.01)
*C07C 47/04* (2006.01)
*C08G 65/30* (2006.01)
*C07D 323/04* (2006.01)
*C08G 65/16* (2006.01)
*C08G 65/06* (2006.01)

(52) U.S. Cl.
CPC .............. *C08G 2/36* (2013.01); *C08G 65/06* (2013.01); *C08G 65/16* (2013.01); *C08G 65/30* (2013.01); *C08G 2650/62* (2013.01)

(56) References Cited

U.S. PATENT DOCUMENTS

| | | |
|---|---|---|
| 3,471,998 A | 10/1969 | Ishida et al. |
| 3,506,615 A | 4/1970 | Chen |
| 3,697,546 A | 10/1972 | Asakawa et al. |
| 3,804,808 A | 4/1974 | Ishii et al. |
| 4,323,502 A | 4/1982 | Muck et al. |
| 4,330,474 A | 5/1982 | Nehring |
| 4,358,623 A | 11/1982 | Murphy et al. |
| 4,420,641 A | 12/1983 | Gerberich et al. |
| 4,450,301 A | 5/1984 | McMillian et al. |
| 4,563,536 A | 1/1986 | Yoshida et al. |
| 4,962,235 A * | 10/1990 | Morishita ............... C07C 45/83 568/492 |
| 4,967,014 A | 10/1990 | Masamoto et al. |
| 5,008,463 A | 4/1991 | Beck et al. |
| 5,508,448 A | 4/1996 | Emig et al. |
| 5,767,294 A | 6/1998 | Steele et al. |
| 5,929,257 A | 7/1999 | Kashihara et al. |
| 6,232,507 B1 | 5/2001 | Kaiser et al. |
| 6,362,305 B1 | 3/2002 | Schweers et al. |
| 6,388,102 B2 | 5/2002 | Schweers et al. |
| 6,448,448 B1 | 9/2002 | Schweers et al. |
| 6,472,566 B2 | 10/2002 | Schweers et al. |
| 6,653,487 B2 | 11/2003 | Schweers et al. |
| 6,781,018 B2 | 8/2004 | Liu et al. |
| 7,301,055 B2 | 11/2007 | Hoffmockel et al. |
| 7,390,932 B2 | 6/2008 | Stroefer et al. |
| 7,598,402 B2 | 10/2009 | Chen et al. |
| 2001/0053865 A1 * | 12/2001 | Schweers .................. C01B 3/22 568/471 |
| 2006/0058537 A1 | 3/2006 | Haubs et al. |
| 2006/0185513 A1 | 8/2006 | Stroefer et al. |
| 2008/0234459 A1 | 9/2008 | Lang et al. |
| 2010/0004409 A1 | 1/2010 | Schwittay et al. |
| 2010/0121081 A1 | 5/2010 | Lang et al. |
| 2010/0145079 A1 | 6/2010 | Stroefer et al. |

FOREIGN PATENT DOCUMENTS

| | | |
|---|---|---|
| DE | 4137846 | 5/1993 |
| DE | 19822598 | 11/1999 |
| GB | 1012372 | 12/1965 |
| GB | 1130513 | 10/1968 |
| GB | 1524440 | 9/1978 |

OTHER PUBLICATIONS

Yamaguchi T. et al: "Synthesis of cyclooligomers of formaldehyde in liquid sulfur dioxide", Chemistry and Industry, vol. 43, Oct. 23, 1971 pp. 1226-1227, XP008149518, Society of Chemical Industry, London; GB ISSN: 0009-3068.
Shoujin Su, Philippe Zaza and Albert Renken: Catalytic Dehydrogenation of Methanol to Water-Free Formaldehyde, Chem. Eng. Technol. 17 (1994) pp. 34-40.
Co pending U.S. Appl. No. 14/359,223, filed May 19, 2014.
Co pending U.S. Appl. No. 14/359,203, filed May 19, 2014.
Co pending U.S. Appl. No. 14/359,319, filed May 20, 2014.
Co pending U.S. Appl. No. 14/359,308, filed May 20, 2014.
Co pending U.S. Appl. No. 14/359,333, filed May 20, 2014.
Co pending U.S. Appl. No. 14/359,594, filed May 21, 2014.
New Jersey Department of Health and Senior Services, Hazardous Substance Fact Sheet. "Boron Trifluoride Diethyl Etherate." (c) Apr. 2000. Available from : < http://nj.gov/health/eoh/rtkweb/documents/fs/0248.pdf>.
Abstract of Japanese Patent -JPH06228126, Aug. 16, 1994, 1 page.
Abstract of Japanese Patent JP2007230979, Sep. 13, 2007, 2 pages.
JP S47-007029 B.
JP S46-031867 B.
JP S37-011033 B.

* cited by examiner

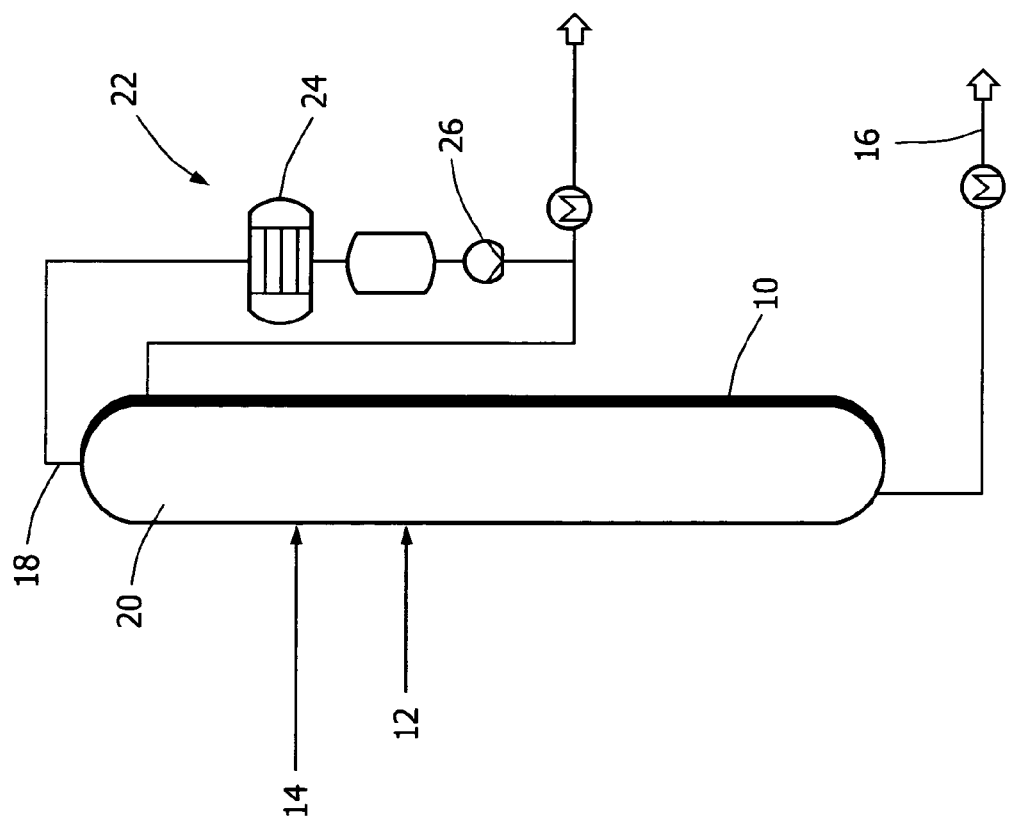

INTEGRATED PROCESS FOR PRODUCING CYCLIC ACETALS AND OXYMETHYLENE POLYMERS

RELATED APPLICATIONS

This present application claims priority to PCT International Patent Application No. PCT/EP2012/073541 having a filing date of Nov. 23, 2012, and which claims filing benefit to European Patent Application No. 11190567.5 filed on Nov. 24, 2011, European Patent Application No. 11190574.1 filed on Nov. 24, 2011, and European Patent Application No. 11190586.5 filed on Nov. 24, 2011, U.S. Provisional Patent Application No. 61/718,393, filed on Oct. 25, 2012 and U.S. Provisional Patent Application No. 61/718,557, filed on Oct. 25, 2012 which are all hereby incorporated by reference in their entirety.

BACKGROUND 1,3,5-Trioxane (hereinafter "trioxane") is the cyclic trimer of formaldehyde. Trioxane is mainly used as a starting material for the manufacturing of polyoxymethylenes (POM) which is a high performance polymer having desirable and exceptional properties in terms of mechanical, chemical and temperature stability. Polyoxymethylene polymers are available as homo- and copolymers.

As the polyoxymethylene market is growing, there is a desire on the side of the trioxane producers to expand their production capacities in order to satisfy the trioxane demand on a competitive basis. The major technical process for the production of trioxane is the conversion of aqueous formaldehyde solutions in the presence of concentrated sulfuric acid as a catalyst. The process for the production of trioxane known in the prior art is complex and comprises an extraction step which necessitates tedious solvent recovery steps. Furthermore, the process conventionally and commercially known in the prior art is time and energy consuming and leads to a low degree of conversion of the formaldehyde source into the desired cyclic acetals. Furthermore, the amount of side products formed by the process is high.

In view of the above, a need currently exists for an efficient process for producing cyclic acetals, such as trioxane. A need also exists for a process for producing cyclic acetals that has a relatively high conversion rate. A need also exists for a process for producing cyclic acetals from different formaldehyde sources.

SUMMARY

In general, the present disclosure is directed to a process for the production of cyclic acetals, which is relatively efficient and/or has relatively high conversion rates. The present disclosure is also directed to producing cyclic acetals with less side products. In one embodiment, the present disclosure is directed to a process in which an alcohol, such as methanol, is converted to cyclic acetals and the formed cyclic acetals may optionally be formed into polyoxymethylene polymers.

In one embodiment, the present disclosure is directed to a process for producing a cyclic acetal. The process includes reacting a formaldehyde source in the presence of a catalyst to produce a cyclic acetal, and wherein the reaction is carried out in a liquid medium comprising a liquid aprotic compound having a boiling point of 120° C. or higher determined at 1 bar, and wherein higher than 20% of the formaldehyde source is converted into the cyclic acetal during the reaction.

In an alternative embodiment, the present disclosure is directed to a process for producing a cyclic acetal that includes the step of reacting a formaldehyde source in the presence of a catalyst to produce a cyclic acetal, and wherein the reaction is carried out in a liquid medium comprising a liquid aprotic compound having a boiling point of 120° C. or higher determined at 1 bar, and wherein the aprotic compound does not chemically react with the formaldehyde source during the reaction.

In another embodiment of the present disclosure, the process for producing a cyclic acetal comprises contacting a formaldehyde source with a liquid medium comprising a sulfur-containing organic compound in the presence of a catalyst; and at least partially converting the formaldehyde source into a cyclic acetal.

In one particular embodiment of the present disclosure, the process for producing a cyclic acetal comprises contacting gaseous formaldehyde with a liquid medium comprising a liquid aprotic compound in the presence of a catalyst; and at least partially converting the gaseous formaldehyde into a cyclic acetal.

The formaldehyde source that is used to produce cyclic acetals in accordance with the present disclosure can come from numerous sources. In one embodiment, the present disclosure is directed to an integrated process in which the formaldehyde source is produced from methanol for a conversion into cyclic acetals. The cyclic acetal can then be used to produce an oxymethylene polymer.

For instance, in one embodiment, the process of the present disclosure includes the steps of converting methanol to a formaldehyde and then contacting the formaldehyde with a catalyst in the presence of an aprotic compound. At least a portion of the formaldehyde is then converted to a cyclic acetal.

In still another embodiment of the present disclosure, a process for producing an oxymethylene polymer comprises the steps of: converting methanol to a formaldehyde; contacting the formaldehyde with a catalyst in the presence of an aprotic compound; at least partly converting the formaldehyde to a cyclic acetal; and polymerizing the cyclic acetal optionally in the presence of a comonomer to form an oxymethylene polymer.

In order to form formaldehyde from methanol, methanol can be subjected to a dehydrogenation process. The dehydrogenation process, for instance, may be non-oxidative. Alternatively, methanol may be oxidized to form the formaldehyde. If desired, formaldehyde produced according to the process may be purified or isolated using extractive distillation.

The aprotic compound that is contacted with the formaldehyde may be in liquid form and may form a homogeneous phase with the formaldehyde as the formaldehyde is converted to the cyclic acetal in the presence of the catalyst. In one embodiment, for instance, the formaldehyde may comprise gaseous formaldehyde that is absorbed by the aprotic compound for contact with the catalyst.

The aprotic compound may be polar. For instance, in one embodiment, the aprotic compound may be dipolar. In one embodiment, the aprotic compound comprises a sulfur containing organic compound such as a sulfoxide, a sulfone, a sulfonate ester, or mixtures thereof. In one embodiment, the aprotic compound comprises sulfolane.

The aprotic compound may also have a relatively high static permittivity or dielectric constant of greater than about 15. The aprotic compound may also be nitro-group free. In particular, compounds having nitro-groups may form undesired side reactions within the process.

In one embodiment, the formaldehyde, the aprotic compound and the catalyst may form a reaction mixture that is primarily comprised of the aprotic compound. As described above, the aprotic compound may be in liquid form when contacted with the formaldehyde. When contacted with the aprotic compound, the formaldehyde may be in gaseous form or may be dissolved in a liquid, such as water to form an aqueous formaldehyde solution. The catalyst may form a homogeneous phase with the aprotic compound or may form a heterogeneous phase with the aprotic compound. For instance, the catalyst may comprise a solid.

Other features and aspects of the present disclosure are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying FIGURES, in which:

FIG. 1 is a schematic diagram of one embodiment of a process in accordance with the present disclosure.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In general, the present disclosure is directed to a process for producing a cyclic acetal by contacting a formaldehyde source with an aprotic compound in the presence of a catalyst. The aprotic compound, for instance, may comprise a liquid dipolar aprotic compound. The aprotic compound can be inert and can have a relative static permittivity of more than about 15. In one embodiment, the aprotic compound may comprise a sulfur-containing organic compound. In one particular embodiment of the present disclosure, a formaldehyde source is first produced from an alcohol, such as methanol. The formaldehyde source, which may comprise gaseous formaldehyde, is then contacted with the aprotic compound in the presence of the catalyst.

As used herein, a formaldehyde source includes formaldehyde and oligomers or polymers formed from formaldehyde. Thus, a formaldehyde source can include paraformaldehyde, oxymethylene homopolymers, and oxymethylene copolymers.

As described above, the formaldehyde source is contacted with an aprotic compound in the presence of a catalyst. The aprotic compound facilitates production of the cyclic acetal in a manner that greatly enhances conversion rates. Of particular advantage, the cyclic acetal produced according to the process can be easily separated from the aprotic compound in the catalyst. For instance, in one embodiment, the cyclic acetal can be separated or isolated from the aprotic compound through a simple distillation process, since the aprotic compound may have a much higher boiling point than the cyclic acetal.

In one embodiment, the aprotic compound is a liquid when contacted with the formaldehyde source. The formaldehyde source may dissolve into the aprotic compound or may be absorbed by the aprotic compound to form a homogeneous phase. The aprotic compound and the catalyst, in one embodiment, may comprise a liquid reaction mixture or a liquid medium.

The formaldehyde source reacts (converts) in the presence of a catalyst. Usually, cationic catalysts, such as Bronsted acids or Lewis acids, accelerate the conversion of the formaldehyde source to the desired cyclic acetals.

The catalyst is a catalyst for the conversion (reaction) of a formaldehyde source into cyclic acetals, in particular into trioxane and/or tetroxane.

Cyclic acetals within the meaning of the present disclosure relate to cyclic acetals derived from formaldehyde. Typical representatives are represented the following formula:

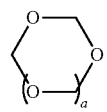

wherein a is an integer ranging from 1 to 3.

Preferably, the cyclic acetals produced by the process of the present disclosure are trioxane (a=1) and/or tetroxane (a=2). Trioxane and tetroxane usually form the major part (at least 80 wt.-%, preferably at least 90 wt.-%) of the cyclic acetals formed by the process of the present disclosure.

The weight ratio of trioxane to tetroxane varies with the catalyst used. Typically, the weight ratio of trioxane to tetroxane ranges from about 3:1 to about 40:1, preferably about 4:1 to about 20:1.

The formaldehyde source used in the process can generally be any compound, oligomer, or polymer that is capable of being converted into a cyclic acetal. The formaldehyde source may be a gas, a liquid, a solid, or mixtures thereof when contacted with the aprotic compound.

The yield and conversion of the formaldehyde source to a cyclic acetal can be improved when water and other protic compounds are absent or present in relatively low amounts. For instance, in one embodiment, the formaldehyde source may contain water and/or other protic compounds in an amount less than about 10,000 ppm, such as less than about 1,000 ppm, such as less than about 100 ppm, such as from about 5 ppm to about 80 ppm, wherein the above concentration refers to the total weight of the formaldehyde source mixture.

It should be understood, however, that conversion rates are still improved even when water and protic compounds are present. For instance, in one embodiment, the formaldehyde source may comprise an aqueous solution containing formaldehyde. For instance, the formaldehyde source may comprise an aqueous formaldehyde solution containing from about 40% to about 90% by weight, such as from about 60% to about 90% by weight, such as from about 65% to about 85% by weight formaldehyde.

Formaldehyde sources that may be used in accordance with the present disclosure include paraformaldehyde, which is a solid. In one embodiment, the paraformaldehyde may dissolve in the aprotic compound.

In an alternative embodiment, the formaldehyde source may comprise a polymer, such as a polyoxymethylene homopolymer or a polyoxymethylene copolymer. In one embodiment, the polymer may have a number average molecular weight (Mn) of more than about 2000 Dalton.

The molar mass is determined by GPC (gel permeation chromatography):
Eluent: hexafluoroisopropanol+0.05% of trifluoroacetic acid potassium salt
Column temperature: 40° C.
Flow rate: 0.5 ml/min
Detector: differential refractometer Agilent 01362A.

The calibration was effected using PMMA standards having a narrow distribution from PSS, with molecular weights of M=505 to M=2 740000. Elution ranges outside this interval were estimated by extrapolation.

The reaction mixture may comprise the formaldehyde source in an amount ranging from about 0.1 to about 80 wt % or about 1 to less than about 80 wt.-%, more preferably from about 5 to about 75 wt %, further preferably ranging from about 10 to about 70 wt % and most preferred ranging from about 20 to about 70 wt %, especially ranging from 30 to 60 wt.-% based on the total weight of the reaction mixture.

It has been found that especially good results in terms of conversion can be achieved when the formaldehyde source is dissolved in a high concentration in the aprotic compound.

Therefore, in a further aspect the amount of formaldehyde source is at least 5 wt-% or at least 10 wt.-%, preferably ranging from 5 to 75 wt.-%, further preferably 10 to 70 wt.-%, especially 15 to 60 wt.-%, based on the total weight of the homogeneous liquid mixture consisting of the formaldehyde source and the aprotic compound.

According to a preferred embodiment the weight ratio of formaldehyde source to aprotic compound is ranging from about 1:1000 to about 4:1, preferably about 1:600 to about 3:1, more preferably about 1:400 to about 2:1, further preferably about 1:200 to about 1:1, especially preferably about 1:100 to about 1:2, particularly about 1:50 to about 1:3, for example about 1:20 to about 1:6 or about 1:15 to about 1:8.

In one particular embodiment, the formaldehyde source may be derived from an alcohol. The alcohol, for instance, may be an alcohol having from about 1 carbon to about 6 carbon atoms in the carbon chain. In one embodiment, for instance, the alcohol may comprise methanol.

A number of processes are known for producing formaldehyde from methanol. For instance, in one embodiment, methanol is oxidized to form formaldehyde. Oxidizing methanol to form formaldehyde typically produces a crude formaldehyde product in which formaldehyde is contained in an aqueous solution. More particularly, the crude formaldehyde typically contains water and unreacted methanol. In one embodiment, the aqueous formaldehyde solution may be contacted with the aprotic compound in the presence of the catalyst to produce a cyclic acetal.

In an alternative embodiment, the crude formaldehyde product may be subjected to extractive distillation in which the formaldehyde is separated from the water and methanol. Through extractive distillation, a substantially anhydrous formaldehyde gas can be produced, collected and converted into a cyclic acetal.

In an alternative embodiment, methanol can be converted into formaldehyde through a dehydrogenation process. The dehydrogenation process may have advantages in certain applications since a virtually water-free formaldehyde may be obtained directly without having to dewater the formaldehyde.

For example, in one embodiment, methanol may dehydrogenated by contacting the methanol with a catalyst at relatively high temperatures. The temperature, for instance, may be from about 300° C. to about 1100° C., such as from about 500° C. to about 1000° C.

Slight Pressure from about 0.5-5 to about 1-3

In one embodiment, dehydrogenation is a non-oxidative process according to the following equation:

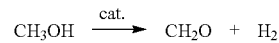

Various different catalysts and mixture of catalysts may be used during the process. The catalyst may be, for instance, an alkali metal and compounds which are gaseous under the reaction conditions. Other catalysts may include alkaline earth metals and various sodium compounds, such as sodium alkoholates, which include sodium methanolate or sodium ethanolate.

Metals that may be used as catalysts include, for example, Li, Na, K, Cs, Mg, Al, In, Ga, Ag, Cu, Zn, Fe, Ni, Co, Mo, Ti, Pt or their compounds. Also suitable are, for example, S, Se, phosphates of transition metals such as V and Fe, and heteropolyacids such as molybdophosphoric acid.

Examples of specific catalysts are sodium or sodium compounds, aluminum oxide, alkali metal aluminate and/or alkaline earth metal aluminate, silver oxide, a catalyst comprising copper, zinc and sulfur, a catalyst comprising copper, zinc and selenium, a catalyst comprising zinc and/or indium, silver, silver, copper and silicon, compounds containing zinc, cadmium, selenium, tellurium or indium.

The form in which such a catalyst, for example a sodium-containing catalyst, is used can vary widely: metallic, e.g. also as an alloy with at least one other alloy constituent, as compound or salt, where at least one nonmetallic element is chemically combined with Na (binary compounds and salts). If more than one element is present in chemically combined form in the compound, a binary, ternary or quaternary compound or salt is present. Use of the catalyst in supported form, for example on an inorganic support, is likewise preferred.

If sodium is used in metallic form, it can be used as solid, liquid or preferably as vapor. Preferred alloys are those with other alkali metals and/or alkaline earth metals, e.g. Ba, Sr, Ca, Cs, Rb, K or particularly preferably Li and/or magnesium.

Furthermore, alloys with B, Al, Si and Sn can also be used. This also applies, in particular, to alloys which can comprise compounds such as sodium boride $NaB_2$, sodium suicide NaSi or NaSn.

Examples of suitable binary sodium compounds and salts are sodium carbides such as $Na_2C_2$, $NaC_8$, sodium halides such as NaF, sodium oxides such as $Na_2O$, sodium azide, sodium phosphide, sodium sulfide, sodium polysulfides, preferably also sodium hydrides such as NaH.

Examples of suitable ternary sodium compounds and salts are sodium borates such as borax, sodium phosphates or hydrogenphosphates, sodium phosphites, sodium (meta)silicates and aluminosilicates, e.g. water glass, $Na_3AlF_6$ (cryolite), sodium (hydrogen)sulfate, sodium sulfite, sodium nitrite, sodium nitrate, sodium amide, sodium acetylide NaCCH, sodium cyanide, sodium thiocyanate, the sodium salt of methyl thiol, sodium thiosulfate, but preferably NaOR where R=H or an organic radical (=salts of organic acids, alkoxides, phenoxides, acetylacetonate, acetoacetic ester salt, salts of salicylic acid or of salicylaldehyde), sodium carbonate and sodium hydrogencarbonate and mixtures thereof, for example soda, thermonatrite, trona, pirssonite, natrocalcite. The use of anhydrous, i.e. dried, salts is generally preferred. Particular preference is given to NaOH, NaOOC—R⁻ (preferably formate, acetate, lactate, oxalate), NaOR' (R' is an organic radical having from 1 to 4 carbon atoms) and sodium carbide. Very particular preference is given to NaOH, sodium formate, sodium methoxide, sodium acetate and sodium carbides such as $Na_2C_2$.

Examples of suitable quaternary compounds are sodium-containing aluminosilicates which can be prepared synthetically or can also occur in a wide variety as natural minerals and rocks (e.g. sodium feldspar or albite and calcium-sodium feldspar or oligoclase). They can additionally be laden with Na by ion exchange.

Use can also advantageously be made of double salts of the alum type or thenardite, glauberite, astrakanite, glaserite, vanthoffite, and the like.

The sodium compounds and salts mentioned here can advantageously also be in the form of mixtures. In particular, it is quite possible to use contents of <50%, preferably <30%, of cations of other alkali metals and/or alkaline earth metals, e.g. Ba, Sr, Ca, Cs, Rb, K or preferably Li and/or magnesium. Industrially available, complex mixtures such as soda lime, ground basic slag and cements, e.g. Portland cement, if desired after enrichment with sodium by storage in sodium-containing solutions (NaCl, sea water) are particularly advantageous.

Particular preference is given to sodium compounds selected from the group consisting of:
a) sodium alkoxides,
b) sodium carboxylates,
c) sodium salts of C—H acid compounds,
d) sodium oxide, sodium hydroxide, sodium nitrite, sodium acetylide, sodium carbide, sodium hydride and sodium carbonyl.

In one embodiment, gaseous methanol can be contacted with multiple catalysts arranged in series. For instance, the process may include a primary catalyst and a secondary catalyst. Through the above process, formaldehyde yields of over 60% and low water concentrations of less than about 5 mol percent per mol of formaldehyde can be obtained at reaction temperatures of from about 600° C. to about 1000° C. Any suitable reactor may be used such as a fixed bed reactor or a fluidized bed reactor. In one embodiment, a carrier gas stream which has been brought to a temperature above the actual reaction temperature may be contacted with the methanol as the methanol is introduced into the reactor. The carrier gas stream may comprise an inert gas such as nitrogen. Alternatively, the carrier gas may comprise a byproduct or a recycled stream from the reactor. In still another embodiment, the carrier gas stream may comprise a reducing gas. For instance, the carrier gas stream may comprise hydrogen gas alone or in combination with carbon monoxide.

As described above, dehydrogenation of methanol can be configured to produce formaldehyde gas that is substantially water-free. Thus, in one embodiment, the formaldehyde gas produced during dehydrogenation can be fed directly to a reactor for converting the formaldehyde into a cyclic acetal. In particular, the formaldehyde gas may be contacted with an aprotic compound in the presence of a catalyst for producing the cyclic acetal, such as trioxane.

In other embodiments, however, the formaldehyde produced from methanol may be collected in crude form. For instance, the collected product may contain formaldehyde combined with water and/or unreacted methanol.

For example, converting methanol to formaldehyde through an oxidation reaction typically produces crude methanol. During oxidation, the methanol is contacted with a catalyst comprising an oxide, such as a metal oxide. Examples of catalysts include, for instance, iron oxide, molybdenum oxide, mixtures thereof and the like. In other embodiments, the catalyst may comprise silver, a silver-based compound, and/or lead.

Aqueous solutions of formaldehyde may, in one embodiment, be fed directly to a reactor for producing a cyclic acetal in accordance with the present disclosure. Yields, however, can be greatly improved if the formaldehyde is first separated from the aqueous solution and fed to the reactor for producing the cyclic acetal. Formaldehyde, however, forms an azeotrope with water at a formaldehyde concentration of greater than about 20% by weight. Consequently, problems have been experienced in separating formaldehyde from water through a simple distillation process.

In this regard, in one embodiment in accordance with the present disclosure, a formaldehyde solution may be fed through an extractive distillation process for recovering substantially anhydrous formaldehyde that then may be converted into a cyclic acetal by contact with an aprotic compound in combination with a catalyst.

During extractive distillation, the crude formaldehyde is fed to the middle or lower part of a distillation column. An extractant is also fed to the distillation column above the crude formaldehyde. The extractant is inert to the formaldehyde but is capable of separating solvents contained with the formaldehyde, such as water. In this manner, purified formaldehyde gas can be collected from the top of the column.

Referring to FIG. 1, for instance, one embodiment of a process for extractive distillation of crude formaldehyde is shown. As illustrated, the process includes a distillation column 10. Crude formaldehyde is fed to the distillation column 10 through one or more ports 12. The crude formaldehyde may comprise formaldehyde and water and optionally methanol. The crude formaldehyde, for instance, may contain formaldehyde in an amount from about 30% to about 90% by weight, such as from about 50% to about 75% by weight. Methanol, on the other hand, may be present in an amount less than about 15% by weight, such as in an amount less than about 10% by weight, such as in an amount less than about 5% by weight. The remainder of the crude formaldehyde comprises water.

The crude formaldehyde is fed to the distillation column 10 generally in a middle portion of the column or towards the bottom portion. The crude formaldehyde may be in liquid form, may be gaseous, or may comprise a mixture of a liquid and gas.

An extractant is also fed to the distillation column 10 through one or more ports 14. The extractant can be inert to the formaldehyde. In one embodiment, the extractant is hydrophilic. The extractant, for instance, may be a solvent for both formaldehyde and water. In general, an extractant is selected that shifts the vapor-liquid equilibrium of the formaldehyde-water solution to the gaseous side of formaldehyde. The extractant also may have a boiling point higher than water (higher than 100° C. at one atmosphere).

The extractant, for instance, may comprise a polyalkylene oxide. In one embodiment, the extractant may comprise a glycol or a glycol ether. Examples of extractants that may be used include diethylene glycol dimethyl ether, triethylene glycol dimethyl ether, tetraethylene glycol dimethyl ether, polyethylene glycol dimethyl ether, or the corresponding diethyl ethers of the above materials. The extractant may also comprise a mixture of the above.

In one embodiment, the extractant may comprise polyethylene glycol dimethyl ether having from about 5 to about 50 ethylene oxide units. The polyethylene glycol dimethyl ether, for instance, may have an average molecular weight of from about 200 to about 2000.

The extractant is fed to the distillation column 10 generally in an amount from about 40 to about 120 times the total weight of water and methanol contained in the crude formaldehyde. Distillation conditions can vary depending upon the composition of the crude formaldehyde, the composition of the purified formaldehyde recovered from the top of the column, and the concentration of extractant fed into the column.

The height of the distillation column and the stage where the crude formaldehyde is to be supplied can be decided from a stage efficiency experimentally obtained from the vapor-liquid equilibrium relationship. The height of the column portion above the stage where the crude formaldehyde is supplied can be increased as the concentration of the crude formaldehyde decreases. Further, in order to increase the recovery of formaldehyde, the height of the column portion below the stage where the crude formaldehyde is supplied may be increased. Hence, the position of feeding the crude formaldehyde is desirably between the middle portion and just above the bottom. The position of feeding the extractant is preferably the top of the column in cases where the extractant has a small vapor pressure, i.e., 50 mmHg or less at 100° C. In cases where the extractant vapor pressure is relatively high, i.e., more than 50 mmHg at 100° C., some height is required above the position of feeding the extractant for recovering the extractant.

The distillation temperature preferably ranges from 80° to 200° C., more preferably 120° to 180° C.

The pressure in the distillation system preferably ranges from normal pressure to 5 kg/cm²G, more preferably 1 kg/cm²G to 3 kg/cm²G.

The extractant having been used for distillation contains water, formaldehyde and other impurities and can be regenerated for recycling. Various methods of regeneration are possible, and a stripping method using an inert gas such as nitrogen under normal pressure or reduced pressure is preferred.

As shown in FIG. 1, the extractant which contains water and other impurities may be collected from the distillation column 10 through an effluent 16.

Purified formaldehyde is recovered from the top 18 of the distillation column 10. Various techniques and processes may be used to further increase the purity of formaldehyde if desired. In FIG. 1, for instance, the distillation column 10 may include a rectifying section 20. The extractant may be fed to the rectifying section.

In one embodiment, the vapor stream leaving the top of the column is condensed fully and fed partly back into the column above the rectifying section by a reflux section 22. The reflux section 22 can include a condenser 24 and a reflux pump 26. In other embodiments, the formaldehyde recovered from the top of the column may be washed or fed through an absorption tower.

Once a formaldehyde source is collected, in accordance with the present disclosure, the formaldehyde source is converted to a cyclic acetal by contacting the formaldehyde source with an aprotic compound and a catalyst. As used herein, an aprotic compound is a compound that does not contain any substantial amounts of hydrogen atoms which can disassociate.

In one embodiment, the aprotic compound is liquid under the reaction conditions. Therefore, the aprotic compound may have a melting point of about 180° C. or less, preferably about 150° C. or less, more preferably about 120° C. or less, especially about 60° C. or less.

For practical reasons, it is advantageous to use an aprotic compound which has a melting point in the order of preference (the lower the melting point the more preferred) of below about 50° C., below about 40° C. and below about 30° C. and below about 20° C. Especially, aprotic compounds which are liquid at about 25 or about 30° C. are suitable since they can be easily transported by pumps within the production plant.

Further, the aprotic compound may have a boiling point of about 120° C. or higher, preferably about 140° C. or higher, more preferably about 160° C. or higher, especially about 180° C. or higher, determined at 1 bar. In a further embodiment the boiling point of the aprotic compound is about 200° C. or higher, preferably about 230° C. or higher, more preferably about 240° C. or higher, further preferably about 250° C. or higher and especially about 260° C. or higher or 270° C. or higher. The higher the boiling point the better the cyclic acetals, especially trioxane and/or tetroxane, formed by the process of the present disclosure can be separated by distillation. Therefore, according to an especially preferred embodiment of the present disclosure the boiling point of the aprotic compound is at least about 20° C. higher than the boiling point of the cyclic acetal formed, in particular at least about 20° C. higher than the boiling point of trioxane and/or tetroxane.

Additionally, aprotic compounds are preferred which do not form an azeotrope with the cyclic acetal, especially do not form an azeotrope with trioxane.

In a preferred embodiment of the present invention, the reaction mixture or liquid medium in the reactor 40 comprises at least about 20 wt.-%, preferably at least about 40 wt.-%, more preferably at least about 60 wt.-%, most preferably at least about 80 wt.-% and especially at least about 90 wt.-% of the aprotic compound(s), wherein the weight is based on the total weight of the reaction mixture. The liquid medium or the reaction mixture or the liquid mixture may comprise one or more aprotic compound(s).

In a preferred embodiment the liquid medium essentially consists of the aprotic compound. Essentially consisting of means that the liquid medium comprises at least about 95 wt.-%, preferably at least about 98 wt.-%, more preferably at least about 99 wt.-%, especially at least about 99.5 wt.-%, in particular at least about 99.9 wt.-% of the aprotic compound(s). In a further embodiment of the invention the liquid medium is the aprotic compound, i.e., the liquid medium is consisting of the aprotic compound.

It has been found that liquid aprotic compounds which at least partly dissolve or absorb the formaldehyde source lead to excellent results in terms of conversion of the formaldehyde source into the desired cyclic acetals.

Therefore, aprotic compounds are preferred which at least partly dissolve or absorb the formaldehyde source under the reaction conditions. Preferred are aprotic compounds which dissolve paraformaldehyde (98 wt.-% formaldehyde, 2 wt.-% water) [can also be expressed as Pn=moles of formaldehyde/moles of water=(98/30)/(2/18)=approx. 29] at the reaction temperature in an amount of at least about 0.1 wt.-%, wherein the weight is based on the total weight of the solution.

The aprotic compound used in the process can be a polar aprotic compound, especially a dipolar compound. Polar aprotic solvents are much more suitable to dissolve the formaldehyde source. Non-polar aprotic compounds such as unsubstituted hydrocarbons (e.g. cyclic hydrocarbons such as cyclohexane, or alicyclic hydrocarbons such as hexane, octane, decane, etc.) or unsubstituted unsaturated hydrocarbons or unsubstituted aromatic compounds are less suitable. Therefore, according to a preferred embodiment the aprotic compound is not an unsubstituted hydrocarbon or unsubstituted unsaturated hydrocarbon or unsubstituted aromatic compound. Further, preferably the reaction mixture comprises unsubstituted hydrocarbons and/or unsubstituted unsaturated hydrocarbons and/or unsubstituted aromatic compounds in an amount of less than about 50 wt.-%, more preferably less than about 25 wt.-%, further preferably less than about 10 wt.-%, especially less than about 5 wt.-%, e.g. less than about 1 wt.-% or about 0 wt.-%.

Halogen containing compounds are less preferred due to environmental aspects and due to their limited capability to dissolve the formaldehyde sources. Further, the halogenated aliphatic compounds may cause corrosions in vessels or pipes of the plant and it is difficult to separate the cyclic acetals formed from the halogenated compounds.

According to one embodiment, the aprotic compound is halogen free. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of halogenated compounds.

Likewise, the use of (liquid) sulphur dioxide leads to difficulties with isolation of the cyclic acetals. Therefore, the aprotic compound is preferably free of sulphur dioxide. In a further preferred embodiment the reaction mixture comprises less than about 50 wt.-%, more preferably less than about 25 wt.-%, further preferably less than 10 wt.-%, more preferably less than 5 wt.-%, especially less than 1 wt.-% or 0 wt.-% of sulphur dioxide.

Polar aprotic compounds are especially preferred. According to a preferred embodiment of the invention the aprotic compound has a relative static permittivity of more than about 15, preferably more than about 16 or more than about 17, further preferably more than about 20, more preferably of more than about 25, especially of more than about 30, determined at 25° C. or in case the aprotic compound has a melting point higher than 25° C. the relative permittivity is determined at the melting point of the aprotic compound.

The relative static permittivity, ∈r, can be measured for static electric fields as follows: first the capacitance of a test capacitor $C_0$, is measured with vacuum between its plates. Then, using the same capacitor and distance between its plates the capacitance $C_x$ with an aprotic compound between the plates is measured. The relative dielectric constant can be then calculated as $$\varepsilon_r = \frac{C_x}{C_0}.$$

Within the meaning of the present invention the relative permittivity is determined at 25° C. or or in case the aprotic compound has a melting point higher than 25° C. the relative permittivity is determined at the melting point of the aprotic compound.

According to a further aspect of the invention the aprotic compound is a dipolar aprotic compound.

The aprotic compound within the meaning of the present invention is generally a dipolar and non-protogenic compound which has a relative permittivity as defined above of more than 15, preferably more than 25 or more than 30, determined at 25° C. or in case the aprotic compound has a melting point higher than 25° C. the relative permittivity is determined at the melting point of the aprotic compound.

The process can be carried out in manner wherein the formaldehyde source is completely dissolved or absorbed in the liquid medium or reaction mixture or liquid mixture (A).

Therefore, according to one embodiment the formaldehyde source and the aprotic compound form a homogenous phase under the reaction conditions.

Suitable aprotic compounds are selected from the group consisting of organic sulfoxides, organic sulfones, organic sulfonate ester, and mixtures thereof.

According to a preferred embodiment the aprotic compound is selected from sulfur containing organic compounds.

Further, the aprotic compound is preferably selected from the group consisting of cyclic or alicyclic organic sulfoxides, alicyclic or cyclic sulfones, and mixtures thereof.

Excellent results can be achieved by aprotic compounds as represented by the following formula (I):

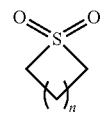
(I)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched. Preferred compounds of formula (I) are sulfolane, methylsulfolane, dimethylsulfolane, ethylsulfolane, diethylsulfolane, propylsulfolane, dipropylsulfolane, butylsulfolane, dibutylsulfolane, pentylsulfolane, dipentylsulfolane, and hexylsulfolane as well as octylsulfolane.

According to the most preferred embodiment the aprotic compound is sulfolane (tetrahydrothiophene-1,1-dioxide).

Sulfolane is an excellent solvent for the formaldehyde source, it is stable under acidic conditions, it does not deactivate the catalysts and it does not form an azeotrope with trioxane. Further, it is a solvent which is inert under the reaction conditions.

Unless indicated otherwise the expression "reaction mixture" refers to the mixture which is used for the reaction of the formaldehyde source to the cyclic acetals. The concentrations and amounts of the individual components of the reaction mixture refer to the concentrations and amounts at the beginning of the reaction. In other words the reaction mixture is defined by the amounts of its starting materials, i.e. the amounts of initial components.

Likewise the amounts defined for the "liquid mixture (A)" refer to the amounts of the components at the beginning of the reaction, i.e. prior to the reaction.

The formaldehyde source reacts to the cyclic acetals and, as a consequence, the concentration of the formaldehyde source decreases while the concentration of the cyclic acetals increases.

At the beginning of the reaction a typical reaction mixture of the invention comprises a formaldehyde source which is at least partly, preferably completely dissolved or absorbed in sulfolane and a catalyst.

Further, an especially preferred embodiment of the present invention is a process for producing cyclic acetal comprising reacting a formaldehyde source in the presence of a catalyst wherein the reaction is carried out in sulfolane or a process for producing cyclic acetal from a formaldehyde source in the presence of a catalyst and sulfolane.

A further preferred aprotic compound is represented by formula (II):

(II)

wherein $R^1$ and $R^2$ are independently selected from $C_1$-$C_8$-alkyl which may be branched or unbranched, preferably wherein $R^1$ and $R^2$ independently represent methyl or ethyl. Especially preferred is dimethyl sulfone.

According to a further preferred embodiment the aprotic compound is represented by formula (III):

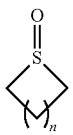
(III)

wherein
n is an integer ranging from 1 to 6, preferably 2 or 3, and wherein the ring carbon atoms may optionally be substituted by one or more substituents, preferably selected from $C_1$-$C_8$-alkyl which may be branched or unbranched.

Suitable aprotic compounds are also represented by formula (IV):

(IV)

wherein $R^3$ and $R^4$ are independently selected from $C_1$-$C_8$-alkyl which may be branched or unbranched, preferably wherein $R^1$ and $R^2$ independently represent methyl or ethyl.

Especially preferred is dimethyl sulfoxide.

In a further aspect of the invention, a mixture of two or more aprotic compounds is used. A mixture of aprotic compounds may be used to decrease the melting point of the aprotic medium. In a preferred embodiment, the aprotic compound comprises or is consisting of a mixture of sulfolane and dimethyl sulfoxide.

The process of the invention is carried out in the presence of a catalyst for the conversion of the formaldehyde source into cyclic acetals. Suitable catalysts are any components which accelerate the conversion of the formaldehyde source to the cyclic acetals.

The catalyst is a catalyst for the conversion (reaction) of a formaldehyde source into cyclic acetals, preferably into trioxane and/or tetroxane.

Usually, cationic catalysts can be used for the process of the invention. The formation of cyclic acetals can be heterogeneously or homogenously catalysed. In case the catalysis is heterogeneous, the liquid mixture comprising the formaldehyde source and the aprotic compound is contacted with the solid catalyst or an immiscible liquid catalyst. A typical liquid immiscible catalyst is a liquid acidic ion exchange resin. Solid catalyst means that the catalyst is at least partly, preferably completely in solid form under the reaction conditions. Typical solid catalysts which may be used for the process of the present invention are acid ion-exchange material, Lewis acids and/or Bronsted acids fixed on a solid support, wherein the support may be an inorganic material such as $SiO_2$ or organic material such as organic polymers.

However, preferred is a homogenous catalysis wherein the catalyst is dissolved in or miscible with the reaction mixture.

Preferred catalysts are selected from the group consisting of Bronsted acids and Lewis acids. The catalyst is preferably selected from the group consisting of trifluoromethanesulfonic acid, perchloric acid, methanesulfonic acid, toluenesulfonic acid and sulfuric acid, or derivatives thereof such as anhydrides or esters or any other derivatives that generate the corresponding acid under the reaction conditions. Lewis acids like boron trifluoride, arsenic pentafluoride can also be used. It is also possible to use mixtures of all the individual catalysts mentioned above.

The catalyst is typically used in an amount ranging from about 0.001 to about 15 wt %, preferably about 0.01 to about 5 wt % or about 0.01 to about 10 wt.-%, more preferably from about 0.05 to about 2 wt % and most preferably from about 0.05 to about 0.5 wt %, based on the total weight of the reaction mixture.

Advantageously, the aprotic compound does not essentially deactivate the catalyst. Generally, the catalysts used for the formation of cyclic acetals from a formaldehyde source are cationic catalysts, such as Bronsted acids or Lewis acids. Preferably, under the reaction conditions the aprotic compound does essentially not deactivate the catalyst used in the process of the present invention. Aprotic solvents such as dimethylformamide (DMF), dimethylacetamide (DMAC) or N-methylpyrrolidone (NMP) are too basic and therefore may deactivate the catalyst and, as a consequence, said solvents are less suitable. According to a preferred embodiment of the present invention the liquid reaction mixture is essentially free of amides, preferably essentially free of acylic or cyclic amides. Essentially free means that the amides may be present in an amount of less than about 5 wt.-%, preferably less than about 2 wt.-%, more preferably less than 0.5 wt.-%, especially less than about 0.01 wt.-% and, in particular, less than 0.001 wt.-% or about 0 wt.-%, wherein the weight is based on the total weight of the liquid reaction mixture.

Nitro group containing compounds can lead to undesired side products or even demonstrate an insufficient solubility for the formaldehyde sources.

Therefore, the aprotic compound preferably does not comprise a nitro group and/or a nitrogen atom. Further, according to a preferred embodiment of the present invention the aprotic compound is a non-aromatic aprotic compound. Especially, the aprotic compound is not nitrobenzene or an aromatic nitro compound. Further, preferably, the aprotic compound does not comprise ether.

Within the meaning of the present invention the aprotic compound does not deactivate the catalyst if under the reaction conditions less than about 95%, preferably less than about 50%, more preferably less than about 10%, of the Bronsted acid catalyst used protonates the aprotic compound. In case a Lewis acid catalyst is used the aprotic compound does not deactivate the catalyst if under the reaction conditions less than about 90 wt-%, preferably less than about 50 wt.-%, more preferably less than about 10 wt-% of the Lewis acid catalyst forms a complex with the aprotic compound.

The degree of protonation and complex formation can be determined by NMR spectroscopy such as $^1$H or $^{13}$C-NMR. The degree of protonation and complex formation is determined at 250° C., preferably in $d_6$-DMSO.

The deactivation of the catalyst can also be determined in the following manner:
10 g of commercially available paraformaldehyde (95 wt %) is dissolved in 100 g of sulfolane at a temperature sufficient to dissolve the paraformaldehyde in such a way that no gaseous formaldehyde can escape. The clear solution is kept at 90° C. and 0.1 wt % of triflic acid is added. The rate of the formation of trioxane is measured (by measuring the concentration of trioxane as a function of time).

The same experiment is repeated, except that 10 g of the sulfolane are replaced by 10 g of the aprotic compound to be tested. If the rate of trioxane formation is still greater than about 1%, preferably greater than about 5%, more preferably greater than about 10%, of the rate of the initial experiment then it is concluded that the aprotic compound in question does not deactivate the catalyst (even though it may reduce its activity).

The aprotic compound should not be too basic in order to avoid deactivation of the catalysts. On the other hand the aprotic compound preferably does not chemically react with the formaldehyde source under the reaction conditions, i.e. is an inert aprotic compound.

Preferably, under the reaction conditions the aprotic compound should not react chemically with the formaldehyde source or the cyclic acetal obtained by the process of the invention. Compounds like water and alcohols are not suitable as they react with formaldehyde. Within the meaning of the present invention an aprotic compound does not chemically react with the formaldehyde source when it meets the following test criteria:
5 g of commercially available paraformaldehyde (95 wt.-%) is added to 100 g of the aprotic compound containing 0.1 wt.-% trifluoromethanesulfonic acid and heated at 120° C. for 1 hour with stirring in a closed vessel so that no gaseous formaldehyde can escape. If less than about 1 wt.-%, preferably less than about 0.5 wt.-%, more preferably less than about 0.1 wt.-% and most preferably less than about 0.01 wt.-% of the aprotic compound has chemically reacted, then the aprotic compound is considered not to have reacted with the formaldehyde source. If the aprotic compound meets the criteria it is considered inert.

Further, under the acidic reaction conditions the aprotic compound should be essentially stable. Therefore, aliphatic ethers or acetals are less suitable as aprotic compounds. The aprotic compound is considered stable under acidic conditions within the meaning of the present invention if the aprotic compound meets the following test conditions:
100 g of the aprotic compound to be tested containing 0.5% by weight (wt.-%) trifluoromethanesulfonic acid is heated at 120° C. for 1 hour. If less than about 0.5 wt.-%, preferably less than about 0.05 wt.-%, more preferably less than about 0.01 wt.-% and most preferably less than about 0.001 wt.-% of the aprotic compound has chemically reacted, then the aprotic compound is considered to be stable under acidic conditions.

It has been found that especially good results in terms of conversion can be achieved when the formaldehyde source is dissolved in a high concentration in the aprotic compound.

Therefore, in a further aspect the amount of formaldehyde source is at least 5 wt.-% or at least 10 wt.-%, preferably ranging from 5 to 75 wt.-%, further preferably 10 to 70 wt.-%, especially 15 to 60 wt.-%, based on the total weight of the homogeneous liquid mixture consisting of the formaldehyde source and the aprotic compound.

According to a preferred embodiment the weight ratio of formaldehyde source to aprotic compound is ranging from about 1:1000 to about 4:1, preferably about 1:600 to about 3:1, more preferably about 1:400 to about 2:1, further preferably about 1:200 to about 1:1, especially preferably about 1:100 to about 1:2, particularly about 1:50 to about 1:3, for example about 1:20 to about 1:6 or about 1:15 to about 1:8.

Typically, the reaction is carried out at a temperature higher than about 0° C., preferably ranging from about 0° C. to about 150° C., more preferably ranging from about 10° C. to about 120° C., further preferably from about 20° C. to about 100° C. and most preferably from about 30° C. to about 90° C.

In a further aspect of the invention the reaction can be carried out at a temperature higher than 0° C., preferably ranging from 0° C. to 200° C., more preferably ranging from 20° C. to 150° C., further preferably ranging from 40° C. to 130° C. and most preferably from 60° C. to 120° C., especially from 80° C. to 120° C. or from 80° C. to 100° C.

The pressure during the reaction can generally be from about 10 millibars to about 20 bars, such as from about 0.5 bar to about 10 bar, such as from about 0.5 bar to about 2 bar.

A further advantageous of the process of the present invention is that the cyclic acetals can easily be separated from the reaction mixture. The cyclic acetal, especially the trioxane can be separated from the reaction mixture by distillation in a high purity grade. Especially in case aprotic compounds (such as sulfolane) having a boiling point higher than about 20° C. above the boiling point of the cyclic acetals is used the formed cyclic acetals can simply be distilled off. In case sulfolane is used as the aprotic compound the formed trioxane can be distilled off without the formation of an azeotrope of sulfolane with trioxane. The process of the invention can be carried out batch wise or as a continuous process.

In a preferred embodiment the process is carried out as a continuous process wherein the formaldehyde source is continuously fed to the liquid medium comprising the catalyst and wherein the cyclic acetals, e.g. the trioxane, is continuously separated (isolated) by separation methods such as distillation.

The process of the invention leads to an extremely high conversion of the formaldehyde source to the desired cyclic acetals.

According to a preferred embodiment the final conversion of the formaldehyde source to the cyclic acetal is greater than 10%, based on initial formaldehyde source.

The final conversion refers to the conversion of the formaldehyde source into the cyclic acetals in the liquid system. The final conversion corresponds to the maximum conversion achieved in the liquid system.

The final conversion of the formaldehyde source to the cyclic acetals can be calculated by dividing the amount of cyclic acetals (expressed in wt.-%, based on the total weight of the reaction mixture) in the reaction mixture at the end of the reaction divided by the amount of formaldehyde source (expressed in wt.-%, based on the total weight of the reaction mixture) at the beginning of the reaction at t=0.

For example the final conversion of the formaldehyde source to trioxane can be calculated as:

Final conversion=(amount of trioxane in the reaction mixture expressed in weight-% at the end of the reaction)/(amount of formaldehyde source in the reaction mixture expressed in weight-% at $t=0$ [initial amount of formaldehyde source in the reaction mixture])

According to a further preferred embodiment of the process of the invention the final conversion of the formaldehyde source into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

According to a further preferred embodiment of the process of the invention the conversion of the formaldehyde source into the cyclic acetals, preferably trioxane and/or tetroxane, is higher than 12%, preferably higher than 14%, more preferably higher than 16%, further preferably higher than 20%, especially higher than 30%, particularly higher than 50%, for example higher than 80% or higher than 90%.

In one embodiment, the cyclic acetal produced according to the present disclosure is then used as a monomer for producing oxymethylene polymers. The oxymethylene polymer, for instance, may comprise a homopolymer or a copolymer.

In one embodiment, for instance, an integrated process may include first converting methanol to a formaldehyde source, contacting the formaldehyde source with an aprotic compound in the presence of a catalyst to produce a cyclic acetal, and then polymerizing the cyclic acetal to produce an oxymethylene polymer. In general, the cyclic acetal can be used to produce any suitable polyoxymethylene polymer in accordance with the present disclosure.

For example, the oxymethylene polymer production process may comprise any suitable process for producing oxymethylene homopolymers and/or copolymers. The polymer production process, for instance, may comprise an anionic polymerization process or a cationic polymerization process. The process for producing the oxymethylene polymer may comprise a heterogeneous process where the polymer precipitates in a liquid, may comprise a homogeneous process such as a bulk polymerization process that forms a molten polymer or may be a polymer process that includes both a heterogeneous phase and a homogeneous phase.

For the preparation of oxymethylene polymers, a monomer that forms —$CH_2$—O— units or a mixture of different monomers, are reacted in the presence of an initiator. Examples of monomers that form —$CH_2$O-units are the cyclic acetals formed according to the present disclosure, such as 1,3,5-trioxane(trioxane) or 1,3,5,7-tetraoxocane.

The oxymethylene polymers are generally unbranched linear polymers which generally contain at least 80 mol %, preferably at least 90 mol %, in particular at least 95 mol %, of oxymethylene units (—$CH_2$—O—). Alongside these, the oxymethylene polymers contain —$(CH_2)_x$-O— units, where x can assume the values from 2 to 25. Small amounts of branching agents can be used if desired. Examples of branching agents used are alcohols whose functionality is three or higher, or their derivatives, preferably tri- to hexahydric alcohols or their derivatives. Preferred derivatives are formulas in which, respectively, two OH groups have been reacted with formaldehyde, other branching agents include monofunctional and/or polyfunctional glycidyl compounds, such as glycidyl ethers. The amount of branching agents is usually not more than 1% by weight, based on the total amount of monomer used for the preparation of the oxymethylene polymers, preferably not more than 0.3% by weight.

Oxymethylene polymers can also contain hydroxyalkylene end groups —O—$(CH_2)_x$—OH, alongside methoxy end groups, where x can assume the values from 2 to 25.

These polymers can be prepared by carrying out the polymerization in the presence of diols of the general formula HO—$(CH_2)_x$—OH, where x can assume the values from 2 to 25. The polymerization in the presence of the diols leads, via chain transfer, to polymers having hydroxyalkylene end groups. The concentration of the diols in the reaction mixture depends on the percentage of the end groups intended to be present in the form of —O—$(CH_2)_x$—OH, and is from 10 ppm by weight to 2 percent by weight.

The molecular weights of these polymers, expressed via the volume melt index MVR, can be adjusted within a wide range. The polymers typically have repeat structural units of the formula —$(CH_2$—O—$)_n$—, where n indicates the average degree of polymerization (number average) and preferably varies in the range from 100 to 10 000, in particular from 500 to 4000.

Oxymethylene polymers can be prepared in which at least 80%, preferably at least 90%, particularly preferably at least 95%, of all of the end groups are alkyl ether groups, in particular methoxy or ethoxy groups.

Comonomers that may be used to produce oxymethylene copolymers including cyclic ethers or cyclic formals. Examples include, for instance, 1,3-dioxolane, diethylene glycol formal, 1,4-butanediol formal, ethylene oxide, propylene 1,2-oxide, butylene 1,2-oxide, butylene 1,3-oxide, 1,3 dioxane, 1,3,6-trioxocane, and the like. In general, one or more of the above comonomers may be present in an amount from about 0.1 to about 20 mol %, such as from about 0.2 to about 10 mol %, based on the amount of trioxane.

The molecular weight of the resultant homo- and copolymers can be adjusted via use of acetals of formaldehyde (chain transfer agents). These also lead to production of etherified end groups of the polymers, and a separate reaction with capping reagents can therefore be omitted. Chain transfer agents used are monomeric or oligomeric acetals of formaldehyde. Preferred chain transfer agents are compounds of the formula I

$$R^1—(O—(CH_2)_q—O—R^2 \quad (I),$$

in which $R^1$ and $R^2$, independently of one another, are monovalent organic radicals, preferably alkyl radicals, such as butyl, propyl, ethyl, and in particular methyl, and q is a whole number from 1 to 50.

Particularly preferred chain transfer agents are compounds of the formula I, in which q=1, very particularly preferably methylal.

The amounts used of the chain transfer agents are usually up to 5000 ppm, preferably from 100 to 3000 ppm, based on the monomer (mixture).

The initiators used can comprise the cationic initiators usually used in the preparation of oxymethylene homo- and copolymers. Examples of these are protic acids, e.g. fluorinated or chlorinated alkyl- and arylsulfonic acids, such as trifluoromethanesulfonic acid, trifluoromethanesulfonic anhydride, or Lewis acids, such as stannic tetrachloride, arsenic pentafluoride, phosphorus pentafluoride, and boron trifluoride, and also their complex compounds, e.g. boron trifluoride etherate, and carbocation sources, such as triphenylmethyl hexafluorophosphate.

In one embodiment, the initiator for cationic polymerization is an isopoly acid or a heteropolyacid or an acid salt thereof which may be dissolved in an alkyl ester of a polybasic carboxylic acid.

The heteropoly acid is a generic term for polyacids formed by the condensation of different kinds of oxo acids through dehydration and contains a mono- or poly-nuclear complex ion wherein a hetero element is present in the center and the oxo acid residues are condensed through oxygen atoms. Such a heteropoly acid is represented by formula (1):

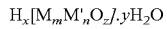 (1)

wherein
M represents an element selected from the group consisting of P, Si, Ge, Sn, As, Sb, U, Mn, Re, Cu, Ni, Ti, Co, Fe, Cr, Th and Ce,
M' represents an element selected from the group consisting of W, Mo, V and Nb,
m is 1 to 10,
n is 6 to 40,
z is 10 to 100,
x is an integer of 1 or above, and
y is 0 to 50.

According to a preferred embodiment of the method according to the present invention the heteropoly acid is a compound represented by the following formula:

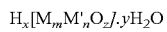

wherein
M represents an element selected from the group consisting of P and Si;
M' represents a coordinating element selected from the group consisting of W, Mo and V;
z is 10 to 100;
m is 1 to 10;
n is 6 to 40;
x is an integer of at least 1; and
y is 0 to 50.

The central element (M) in the formula described above may be composed of one or more kinds of elements selected from P and Si and the coordinate element (M') may be composed of at least one element selected from W Mo and V, particularly preferably W or Mo.

Further, acidic salts of heteropoly acids each having a form, in which any of the various metals substitutes for a part of H's (hydrogen atoms) in the formula (1) can also be used as the initiator.

Specific examples of heteropoly acids are selected from the group consisting of phosphomolybdic acid, phosphotungstic acid, phosphomolybdotungstic acid, phosphomolybdovanadic acid, phosphomolybdotungstovanadic acid, phosphotungstovanadic acid, silicotu ngstic acid, silicomolybdic acid, silicomolybdotungstic acid, silicomolybdotungstovanadic acid and acid salts thereof.

Excellent results have been achieved with heteropoly acids selected from 12-molybdophosphoric acid ($H_3PMO_{12}O_{40}$) and 12-tungstophosphoric acid ($H_3PW_{12}O_{40}$) and mixtures thereof.

The amount of the heteropoly acid or the acid salt thereof to be used as a initiator for the polymerization of a monomer component, which forms —$CH_2$—O-units is 0.1 to 1000 ppm, preferably 0.2 to 40 ppm, more preferably 0.3 to 5 ppm based on the total amount of the monomer component.

In another embodiment, the initiator for cationic polymerization comprises at least one protic acid and at least one salt of a protic acid, wherein said at least one protic acid is sulfuric acid, tetrafluoroboric acid, perchloric acid, fluorinated alkyl sulfonic acid, chlorinated alkyl sulfonic acid or aryl sulfonic acid, and wherein said salt of protic acid is an alkali metal or alkaline earth metal salt of protic acid and/or a substituted ammonium salt of protic acid, the cations of the ammonium salt having the general formula (I)

where $R^1$-$R^4$ are independently hydrogen, an alkyl group or an aryl group.

Particular preference is given to substituted ammonium ions having the general formula (I)

where $R^1$ to $R^4$ are independently hydrogen, an alkyl group such as methyl, ethyl, n-propyl, isopropyl, n-butyl, isobutyl or an aryl group such as phenyl or 4-methoxypheny.

Substituted ammonium ions are also preferred because the corresponding salts are very simple to prepare by mixing the protic acid with the corresponding amine. Thus, mixing triethylamine and trifluoromethanesulfonic acid forms triethylammonium triflate.

Useful organic cations further include protonated nitrogenous compounds, examples being protonated imidazole and protonated amides. Useful amides include for example dimethylformamide, dimethylacetamide and N-methylpyrrolidone.

The anions of the salts are chosen for low nucleophilicity and good thermal stability. Examples are perchlorate, tetrafluoroborate, tetraphenylborate, hexafluorophosphate and the preferred trifluorometha nesulfonate.

The molar ratio of protic acid to salt can be varied within a wide window. In principle, molar ratios of protic acid to salt in the range from 1:0.01 to 1:2000 are possible, preferably in the range from 1:0.5 to 1:10, more preferably in the range from 1:0.8 to 1:8 and most preferably in the range from 1:1 to 1:4.

The amount of the above initiator used is in the range from $10^{-6}$% by weight to 1% by weight, preferably in the range from $10^{-5}$% by weight to $10^{-3}$% by weight and more preferably in the range from $2\times10^{-5}$% by weight to $5\times10^{-4}$% by weight, based on the total weight of monomers used. The amount of initiator used depends on the chemical composition of the protic acid and the chemical composition of the monomers or monomer mixture. For example, typically less initiator is used for homopolymerizing 1,3,5-trioxane than for copolymerizing trioxane with dioxolane.

In order to terminate the polymerization, the reaction mixture, which still comprises unconverted monomers and/or byproducts, such as trioxane and formaldehyde, alongside polymer, is brought into contact with deactivators. These can be added in bulk form or a form diluted with an inert solvent to the polymerization mixture. The result is rapid and complete deactivation of the active chain ends.

Deactivators that can be used are those compounds which react with the active chain ends in such a way as to terminate the polymerization reaction. Examples are the organic bases triethylamine or melamine, and also the inorganic bases potassium carbonate or sodium acetate. It is also possible to use very weak organic bases, such as carboxamides, e.g.

dimethylformamide. Tertiary bases are particularly preferred, examples being triethylamine and hexamethylmelamine.

The concentrations used of the bases are preferably from 1 ppm to 1% by weight, based on the polymerization material. Concentrations of from 10 ppm to 5000 ppm are preferred.

The present disclosure may be better understood with respect to the following example.

Example 1

Anhydrous formaldehyde was prepared by the thermal decomposition of paraformaldehyde (essay: 96 wt %, from Acros Organics) at a rate of ca. 1 g/min at appr. 120° C. and a pressure of 80 mbar. The formaldehyde gas was absorbed in a absorption column containing 500 g sulfolane (<0.1 wt % water) with 0.1 wt % triflic acid at around 40° C. After 1 hr, the sulfolane in the adsorption column was neutralized with triethylamine and analyzed by GC and sulfite titration. The following composition was found:
Trioxane: 8.3 wt %
Tetroxane: 1.1 wt %
Formaldehyde: 0.6 wt %
Methyl formate: 0.5 wt %
Final conversion of formaldehyde to trioxane in the reaction mixture:
77.5%
Final conversion of formaldehyde to trioxane and tetroxane in the reaction mixture:
88%

Example 2

Anhydrous formaldehyde was prepared by the thermal decomposition of paraformaldehyde at a rate of 1 g/min. The formaldehyde gas was absorbed in a absorption column containing 500 g sulfolane (<0.1 wt.-% water) with 0.1 wt.-% trifluoromethanesulfonic acid. The reaction is carried out in a temperature range from 30 to 40° C. After 50 min the sulfolane in the adsorption column was analysed by gas chromatography (GC) and sulfite titration. The following composition was found:
Trioxane: 6.8 wt %
Tetroxane: 0.9 wt %
Formaldehyde: 1.1 wt %
Methyl formate: 0.7 wt %
Final conversion of formaldehyde to trioxane in the reaction mixture: 71.6%
Final conversion of formaldehyde to trioxane and tetroxane in the reaction mixture: 81.1%

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for producing a cyclic acetal comprising:
    converting methanol to a formaldehyde;
    contacting the formaldehyde with a catalyst in the presence of an aprotic compound, the aprotic compound comprising a sulfur containing organic compound having a boiling point greater than 120° C. determined at 1 bar; and
    at least partly converting the formaldehyde to a cyclic acetal.

2. A process according to claim 1, wherein the methanol is dehydrogenated in order to form the formaldehyde.

3. A process according to claim 1, wherein the formaldehyde is formed by nonoxidative dehydrogenation of methanol.

4. A process according to claim 1, wherein the formaldehyde is formed by dehydrogenating methanol at a temperature of from about 300° C. to about 1100° C.

5. A process according to claim 1, wherein the formaldehyde is formed in the presence of a catalyst comprising an alkali metal, an alkaline earth metal, copper, zinc, tin, compounds thereof, or mixtures thereof.

6. A process according to claim 1, wherein the formaldehyde is formed by extractive distillation.

7. A process according to claim 1, wherein the methanol is oxidized to form the formaldehyde.

8. A process according to claim 6, wherein the extractive distillation is carried out by feeding crude formaldehyde containing water and methanol to a middle or lower part of a distillation column and feeding an extractant to an upper part of the distillation column, the extractant being inert to formaldehyde, and wherein formaldehyde gas is collected from a top of the distillation column.

9. A process according to claim 8, wherein the extractant comprises diethylene glycol dimethyl ether, triethylene glycol dimethyl ether, tetraethylene glycol dimethyl ether, polyethylene glycol dimethyl ether having from about 5 ethylene oxide units to about 50 ethylene oxide units, corresponding diethylene ethers of the above or mixtures thereof.

10. A process according to claim 1, wherein the formaldehyde is gaseous formaldehyde when contacted with the aprotic compound.

11. A process according to claim 1, wherein the aprotic compound has a boiling point of greater than about 140° C. determined at one bar.

12. A process according to claim 1, wherein the formaldehyde, the aprotic compound and the catalyst form a reaction mixture and wherein the reaction mixture comprises at least 60 wt.-%, of the aprotic compound, wherein the weight is based on the total weight of the reaction mixture.

13. A process according to claim 1, wherein the aprotic compound comprises a dipolar nitro-group free compound.

14. A process according to claim 1, wherein the aprotic compound is represented by formula (I):

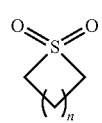

(I)

wherein
n is an integer ranging from 1 to 6, and
wherein the ring carbon atoms may optionally be substituted by one or more substituents, selected from $C_1$-$C_8$-alkyl which may be branched or unbranched.

15. A process according to claim 1 wherein the aprotic compound is sulfolane.

16. A process according to claim 1 wherein the aprotic compound is represented by formula (II):

(II)

wherein $R^1$ and $R^2$ are independently selected from $C_1$-$C_8$-alkyl which may be branched or unbranched.

17. A process according to claim 1 wherein the aprotic compound is represented by formula (III):

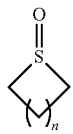

(III)

wherein
n is an integer ranging from 1 to 6, and
wherein the ring carbon atoms may optionally be substituted by one or more substituents, selected from $C_1$-$C_8$-alkyl which may be branched or unbranched; or
the aprotic compound is represented by formula (IV):

(IV)

wherein $R^3$ and $R^4$ are independently selected from $C_1$-$C_8$-alkyl which may be branched or unbranched.

18. A process according to claim 1 wherein the formaldehyde and the aprotic compound form a homogenous phase.

19. A process according to claim 1 wherein the conversion to the cyclic acetal is carried out at a temperature ranging from 20° C. to 150° C., and is carried out at a pressure of from 10 millibars to 10 bars.

20. A process according to claim 9, wherein the extractant comprises sulfolane.

* * * * *